United States Patent [19]

Akhavan-Tafti et al.

[11] Patent Number: 5,601,977
[45] Date of Patent: *Feb. 11, 1997

[54] ENZYME-CATALYZED CHEMILUMINESCENT DETECTION OF PROTEINS AND NUCLEIC ACIDS USING HYDROXYARYL CYCLIC DIACYLHYDRAZIDE COMPOUNDS

[75] Inventors: Hashem Akhavan-Tafti, Sterling Heights; Richard S. Handley, Canton, both of Mich.

[73] Assignee: Lumigen, Inc., Southfield, Mich.

[ * ] Notice: The term of this patent shall not extend beyond the expiration date of Pat. No. 5,552,298.

[21] Appl. No.: 996,110

[22] Filed: Dec. 23, 1992

Related U.S. Application Data

[63] Continuation-in-part of Ser. No. 965,231, Oct. 23, 1992.
[51] Int. Cl.⁶ .................................................. C12Q 1/68
[52] U.S. Cl. .................... 435/6; 436/501; 436/172; 436/819
[58] Field of Search ...................... 435/6, 7.1, 7.5, 435/968; 436/501, 172, 819

[56] References Cited

U.S. PATENT DOCUMENTS

| | | | |
|---|---|---|---|
| 4,614,712 | 9/1986 | Baldwin et al. | 435/4 |
| 4,794,073 | 12/1988 | Dattagupta et al. | 435/6 |
| 4,927,769 | 5/1990 | Chang et al. | 436/518 |

FOREIGN PATENT DOCUMENTS 2237383  1/1991  United Kingdom .

OTHER PUBLICATIONS

Conyers, S. M., et al., Analytical Biochemistry 192 207–211 (1991).
Akhavan–Tafti, H., et al., Bioluminescence and Chemiluminescence 199–202 (1994).
Motsenbocker, M. A., J. Biolumin Chemilumin 9 15–20 (1994).
Cercek, B., et al., J. Biolumin. Chemilumin 9 273–277 (1994).
Vlasenko, S. B., et al., J. of Bioluminescence and Chemiluminescence 4 164–176 (1989).
Misra, H. P., et al., Archives of Biochemistry and Biophysics 215, No. 1, pp. 59–65 (1982).
Egorov, A. M., et al., Chemiluminescent and Bioluminescent Assays 186–290 (1993).
Whitehead, T. P., et al., Bioluminescence and Chemiluminescence, 425–429 (1993).
Kricka et al., in *Luminescence Immunoassay & Molecular Applications*, CRC Press, 1990, pp. 78–98.
Würzberg et al., J. Phys. Chem. 83(21), 2687–2692 (1979).
Heinicke, et al., J. Immun. Meth., 152 (1992), 227–236.
I. E. Kalinichenko, A. T. Pilipenko, V. A. Barovskii, Ukr. Khim. Zh. (Russ. Ed.), 43(10), 1102–1106 (1977).
Kalinichenko, I. E., Barovskii, V. A., Pilipenko, A. T., Ukr. Khim. Zh. (Russ. Ed.), 44(7), 748–752 (1978).
A. T. Pilipenko, V. A. Barovskii, I. E. Kalinichenko, Zh. Anal. Khim., 33 (10), 1880–1884 (1978).
I. E. Kalinichenko, V. A. Barovskii, Ukr. Khim. Zh. (Russ. Ed.), 45(1), 58–62 (1979).
I. E. Kalinichenko, T. M. Tkachuk, A. T. Pilipenko, Zh. Anal. Khim., 39 (7), 1281–1284 (1984).
K. D. Gundermann, W. Horstmann, G. Bergman, Lieb. Ann. der Chem, 684, 127–141 (1965).
R. B. Brundett, D. F. Roswell, E. H. White, J. Am. Chem. Soc., 94, 7536 (1972).
H. R. Schroeder, P. O. Bogelhut, R. J. Carrico, R. C. Boguslaski, R. T. Buckler, Anal. Chem. 48, 1933 (1976).
H. R. Schroeder in Luminescent Immunoassays: Perspectives in Endocrinology and Clinical Chemistry, M. Serio and M. Pazzagli, Eds., Raven Press, NY, pp. 129–146 (1982).
M. Pazzagli, G. Messeri, A. L. Caldini, G. Monetti, G. Martinazzo, M. Serio, J. Steroid Biochem., 19, 407 (1983).
J. DeBoever, F. Kohen and D. Vandekerckhove in Bioluminescence and Chemiluminescence New Perspectives, J. Scholmerich et al., Eds., J. Wiley & Sons, Chichester, pp. 257–260 (1987).
T. P. Whitehead, G. H. Thorpe, T. J. Carter, C. Groucutt, L. J. Kricka, Nature, 305, 158 (1983).
G. H. Thorpe, L. J. Kricka, S. B. Mosely, T. P. Whitehead, Clin. Chem., 31, 1335 (1985).
K. Tanabe, T. Kawasaki, M. Maeda, A. Tsuji, M. Yabuuchi, Bunseki Kagaku, 36, 82 (1987).
A. Tsuji, M. Maeda, H. Arakawa, Anal. Sci., 5 497 (1989).
K. Sasamoto, Y. Ohkura, Chem. Pharm. Bull. 38 (5), 1323 (1990).
K. Sasamoto, Y. Ohkura, Chem. Pharm. Bull. 39 (2), 411 (1991).
G. H. Thorpe, S. B. Mosely, L. J. Kricka, R. A. Stott, T. P. Whitehead, Anal. Chim. Acta, 170, 107 (1985).
J. A. Matthews, A. Batki, C. Hynds, L. J. Kricka, Anal. Biochem., 151, 205, (1985).
Y. Omote, H. Yamamoto, N. Sugiyama, Chem. Commun., 914 (1970).
R. A. W. Stott, L. J. Kricka, in Bioluminescence and Chemiluminescence New Perspectives, J. Scholmerich et al Eds., John Wiley & Sons, Chichester, England, 237–240 (1987).
U. K. Laemmli, London, Nature vol. 227 pp. 680–685.

*Primary Examiner*—Stephanie W. Zitomer
*Assistant Examiner*—Scott W. Houtteman
*Attorney, Agent, or Firm*—Ian C. McLeod

[57] ABSTRACT

A method and test kit using a hydroxyaryl cyclic diacylhydrazide, a peroxide and a peroxidase enzyme on a blotting membrane for detecting DNA, RNA or proteins (polypeptides) is described. The method and kit provides enhanced chemiluminescence in an assay because of the use of the membrane. The method and test kit is particularly useful in Western, Southern and Northern blotting type assays and DNA sequencing.

39 Claims, 4 Drawing Sheets

1 2 3 4 5

5 4 3 2 1

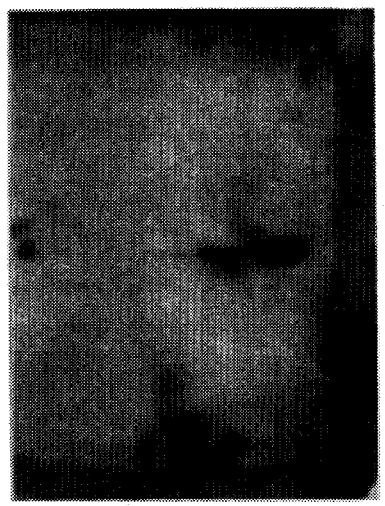 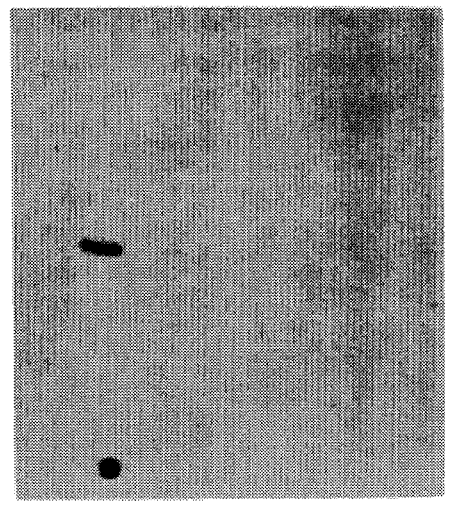
5 4 3 2 1
FIG. 2A
1 2 3 4 5
FIG. 2B 1 2 3

ENZYME-CATALYZED CHEMILUMINESCENT DETECTION OF PROTEINS AND NUCLEIC ACIDS USING HYDROXYARYL CYCLIC DIACYLHYDRAZIDE COMPOUNDS

CROSS-REFERENCE TO RELATED APPLICATION

This application is a continuation-in-part of U.S. application Ser. No. 965,231, filed October 23, 1992.

BACKGROUND OF THE INVENTION (1) State of The Invention

This invention relates to a method of generating light chemically (chemiluminescence) in an assay on a surface such as a membrane by the action of a peroxidase enzyme with an oxidant such as hydrogen peroxide on a group of hydroxyaryl cyclic diacylhydrazides. The invention also relates to a method of greatly increasing the amount of chemiluminescence produced from this process by the use of specific enhancers and by conducting the reaction on a membrane. The invention also relates to the use of this method to detect the peroxidase enzyme. Further, the invention relates to the use of the method to detect and quantitate various biological molecules. For example, the method may be used to detect haptens, antigens and antibodies by the technique of immunoassay, proteins by Western blotting, DNA and RNA by Southern and Northern blotting, respectively. The method may also be used to detect RNA and DNA in dot blots, DNA in sequencing applications, and DNA in DNA probe assays.

(2) Prior Art a. Chemiluminescent Oxidation of Hydroxyaryl Cyclic Diacylhydrazides.

A series of reports has appeared concerning the chemiluminescent reactions of 3- or 4-hydroxyphthalhydrazide with different chemical oxidizing agents (I. E. Kalinichenko, A. T. Pilipenko, V. A. Barovskii, Ukr. Khim. Zh. (Russ. Ed.), 43(10), 1102–6 (1977); Kalinichenko, I. E., Barovskii, V. A., Pilipenko, A. T., Ukr. Khim. Zh. (Russ. Ed.), 44(7), 748–52 (1978); A. T. Pilipenko, V. A. Barovskii, I.E. Kalinichenko, Zh. Anal. Khim., 33(10), 1880–4 (1978); I. E. Kalinichenko, V. A. Barovskii, Ukr. Khim. Zh. (Russ. Ed.), 45(1), 58–62 (1979); I. E. Kalinichenko, T. M. Tkachuk, A. T. Pilipenko, Zh. Anal. Khim., 39(7), 1281–4 (1984)). Gundermann reports the chemiluminescent oxidation of 7-hydroxynaphthalene-1,2-dicarboxylic hydrazide in aqueous solution with hydrogen peroxide and a metal catalyst (K.-D. Gundermann, W. Horstmann, G. Bergman, Lieb. Ann. der Chem, 684, 127–141 (1965)). No reports are known concerning the use of hydroxyaryl cyclic diacylhydrazides with a peroxidase enzyme or any enzyme to generate chemiluminescence. Further, there are no known reports of the use of hydroxyaryl cyclic diacylhydrazides to generate chemiluminescence for the detection of biological compounds.

b. Chemiluminescent Oxidation of Luminol and Related Compounds.

Aminoaryl cyclic diacylhydrazides such as luminol and isoluminol react with $H_2O_2$ and a peroxidase enzyme catalyst (such as horseradish peroxidase, HRP) under basic conditions with emission of light. The reaction is also catalyzed by small amounts of several metal ions including Fe(III), Cu(II) and Cr(III) or iron-containing organic compounds (e.g. R. B. Brundett, D. F. Roswell, E. H. White, J. Am. Chem. Soc., 94, 7536 (1972)). This reaction has been used as the basis for analytical methods for the detection of $H_2O_2$ and for metal ions. Luminol and isoluminol may be directly conjugated to a species to be detected. The first chemiluminescent immunoassay using luminol as a label was reported by Schroeder for an assay of biotin. (H. R. Schroeder, P. O. Vogelhut, R. J. Carrico, R. C. Boguslaski, R. T. Buckler, Anal. Chem. 48, 1933 (1976)). Several applications of the use of luminol derivatives as labels have been reported since then (H. R. Schroeder in Luminescent Immunoassays: Perspectives in Endocrinology and Clinical Chemistry, M. Serio and M. Pazzagli, Eds., Raven Press, New York, pp 129–146 (1982); M. Pazzagli, G. Messeri, A. L. Caldini, G. Monetti, G. Martinazzo, M. Serio, J. Steroid Biochem., 19, 407 (1983); J. DeBoever, F. Kohen and D. Vandekerckhove in Bioluminescence and Chemiluminescence New Perspectives, J. Scholmerich, et al., Eds., J. Wiley & Sons, Chichester, pp 257–260 (1987)). Various enhancers have also been employed in conjunction with horseradish peroxidase in the oxidation of luminol to increase the intensity of light emitted. These include, for example, D-luciferin (T. P. Whitehead, G. H. Thorpe, T. J. Carter, C. Groucutt, L. J. Kricka, Nature, 305, 158 (1983)) and p-iodophenol and p-phenylphenol (G. H. Thorpe, L. J. Kricka, S. B. Mosely, T. P. Whitehead, Clin. Chem., 31, 1335 (1985)).

c. Enzyme-Catalyzed Chemiluminescent Reactions (1) Enzymatic Generation of Hydrogen Peroxide. Various enzymatic reaction schemes are known which produce hydrogen peroxide. The generated hydrogen peroxide can, in turn, be used to oxidize a compound which emits light. For example, glucose oxidase reacts with $O_2$ and sucrose to produce $H_2O_2$. Similarly, amino acid oxidase and cholesterol oxidase react with amino acids or cholesterol, respectively, and $O_2$ to produce $H_2O_2$. Examples of compounds which are oxidized by hydrogen peroxide to produce light are luminol and isoluminol, lucigenin, esters of N-methylacridine and esters or amides of oxalic acid. Glucose-6-phosphate dehydrogenase and galactose-6-phosphate dehydrogenase have been used to produce $H_2O_2$ indirectly by reduction of oxygen through an electron-relay system (K. Tanabe, T. Kawasaki, M. Maeda, A. Tsuji, M. Yabuuchi, Bunseki Kagaku, 36, 82 (1987); and A. Tsuji, M. Maeda, H. Arakawa, Anal. Sci., 5 497 (1989)).

(2) Enzymatic Deprotection of a Luminol Derivative. The compound o-aminophthalhydrazide-N- acetyl-β-D-glucosaminide (luminol-NAG) and 4'-(6'-diethylaminobenzofuranyl)phthalhydrazide-N-acetyl-β-D-glucosaminide are substrates for the enzyme N-acetyl-β-D-glucosaminidase which serve as a masked form of luminol. Upon action of the enzyme on these substrates, luminol or a luminol derivative are liberated which may be detected as described above (K. Sasamoto, Y. Ohkura, Chem. Pharm. Bull. 38(5), 1323 (1990); K. Sasamoto, Y. Ohkura, Chem. Pharm. Bull. 39(2), 411 (1991)).

d. Use of Chemiluminescence in DNA Hybridization assays.

Biological assays such as enzyme immunoassays and DNA probe assays involving enzymes utilize a wide variety of substrates which either form a color (chromogenic), become fluorescent (fluorogenic) or emit light (chemiluminogenic) upon reaction with the enzyme. Of these three choices, chemiluminescence offers the greatest sensitivity. In an assay, the enzyme (reporter enzyme) is conjugated or bound to the molecule to be detected or to some other substance capable of selectively binding or associating with the molecule to be detected. Once the bound reporter enzyme is separated from unbound enzyme, a substrate is provided with which the reporter enzyme generates a signal.

The enzyme horseradish peroxidase has been widely used in enzyme immunoassays and DNA hybridization assays with chemiluminescent detection using luminol or isoluminol as substrate (T. P. Whitehead, G. H. Thorpe, T. J. Carter, C. Groucutt, L. J. Kricka, Nature, 305, 158 (1983); G. H. Thorpe, L. J. Kricka, S. B. Mosely, T. P. Whitehead, Clin. Chem., 31, 1335 (1985); G. H. Thorpe, S. B. Mosely, L. J. Kricka, R. A. Stott, T. P. Whitehead, Anal. Chim. Acta, 170, 107 (1985); J. A. Matthews, A. Batki, C Hynds, L. J. Kricka, Anal. Biochem., 151, 205, (1985)). Commercially available kits for conjugation of HRP with enhanced luminol chemiluminescent detection are sold under the tradename "AMERLITE™" (Amersham International, PLC., Amersham, England).

OBJECTS

It is therefore an object of the present invention to provide a method and hydroxyaryl cyclic diacylhydrazides for use in generating chemiluminescence by the action of a peroxidase enzyme and a phenol enhancer for the detection of biological materials and compounds. It is also an object of the present invention to provide a method and kit using hydroxyaryl cyclic diacylhydrazides on membranes for generating chemiluminescence by the action of a peroxidase enzyme and a phenol enhancer for the detection of peroxidase enzymes and enzyme-conjugates. Additionally, it is an object of the present invention to provide a method and kit using hydroxyaryl cyclic diacylhydrazides on surfaces such as membranes for generating chemiluminescence by the action of a peroxidase enzyme and a phenol enhancer for detection of nucleic acid assays in solution and on surfaces. Further, it is an object of the present invention to provide a method and kit using hydroxyaryl cyclic diacylhydrazides for generating chemiluminescence by the action of a peroxidase enzyme and a phenol enhancer, for detection of proteins in Western blots and nucleic acids in Northern blots, Southern blots and other DNA hybridization assays.

IN THE DRAWINGS

FIG. 1 shows the result of a Western blot analysis of human transferrin on PVDF membrane (IMMOBILON P) with chemiluminescent detection using fractionated goat anti-human transferrin serum, rabbit anti-goat IgG-peroxidase conjugate, NaBO$_3$ and 5-hydroxy2,3-dihydrophthalazine-1,4-dione. Human transferrin loaded into each slot was (1) 5000 pg, (2) 1000 pg, (3) 200 pg, (4) 50 pg and (5) 10 pg. The blots were exposed to X-OMAT AR x-ray film (A) for one minute after a 20 minute incubation or to OMC x-ray film (B) for 10 minutes after a 30 minute incubation.

FIG. 2 shows the result of a Western blot analysis of human transferrin on nitrocellulose with chemiluminescent detection using fractionated goat anti-human transferrin serum, rabbit anti-goat IgG-peroxidase conjugate, NaBO$_3$ and 5-hydroxy-2,3-dihydrophthalazine1,4-dione. Human transferrin loaded into each slot was (1) 5000 pg, (2) 1000 pg, (3) 200 pg, (4) 50 pg and (5) 10 pg. The blots were exposed to X-OMAT AR x-ray film (A) for one minute after an 8 minute incubation or to OMC x-ray film (B) for 60 minutes after a 45 minute incubation.

FIG. 3 shows the result of a dot blot analysis of biotinylated lambda DNA/Hind III fragments bound to avidin-horseradish peroxidase with chemiluminescent detection using a detection reagent containing 5-hydroxy-2,3-dihydrophthalazine-1,4-dione. Biotinylated lambda DNA/Hind III fragments in 6×SSC containing 100 µg/mL herring sperm DNA were dotted on nitrocellulose (A) or "IMMOBILON™-P" (B) in 15 ng, 1.5 ng, 150 pg, 15 pg and 1.5 pg quantities. 150 ng herring sperm DNA in 6×SSC was dotted. The blots were exposed to x-ray film for three minutes. The two columns of spots on the left in FIG. 3 A and B represent dilutions of biotinylated lambda DNA/Hind III fragments containing 150 ng of herring sperm DNA. The control spots are only 150 ng of herring sperm DNA.

FIG. 4 shows the result of a Southern blot analysis of a single copy gene, proto-oncogene mos with chemiluminescent detection of a horseradish peroxidase conjugated probe using a detection reagent containing 5-hydroxy-2,3-dihydrophthalazine-1,4-dione. The EcoR1 restricted mouse genomic DNA loaded in slots 1 and 2 was 20 micrograms. 95 ng of lambda DNA/Hind III fragments (Life Technologies, Inc.) was loaded in slot 3. The blots were exposed to x-ray film for two minutes.

DESCRIPTION OF PREFERRED EMBODIMENTS

Figure 1A:
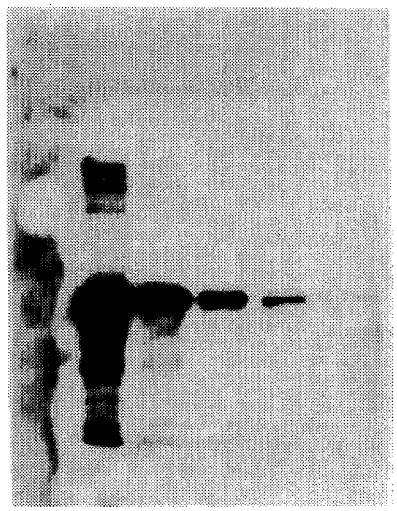

The present invention relates to an improvement in a method for detecting a member of a specific binding pair labeled with a peroxidase enzyme in an assay procedure by a chemiluminescent reaction, which comprises the chemiluminescent reaction caused by reacting with the binding pair on a membrane with a hydroxyaryl cyclic diacylhydrazide of the formula:

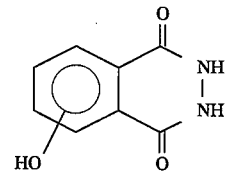

and a peroxide so that light is produced for detecting the analyte.

Further, the present invention relates to a kit for detecting a nucleic acid or a fragment of a nucleic acid comprising: an oligonucleotide probe complementary to the nucleic acid or a portion thereof labeled with a peroxidase enzyme; a hydroxyaryl cyclic diacylhydrazide compound of the formula:

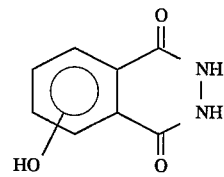

a phenolic enhancer compound in an amount which enhances light production from the diacylhydrazide in the presence of the peroxidase enzyme and decreases background chemiluminescence; a peroxide compound in an amount which reacts with the diacylhydrazide in the presence of the peroxidase; a chelating agent in an amount which prevents the peroxide compound from activating the diacylhydrazide prior to reaction with the peroxidase; and a water-soluble chemiluminescence-enhancing substance; and a membrane on which the hybridization is performed.

Further, the present invention relates to a kit for detecting a nucleic acid or a fragment of a nucleic acid comprising: an oligonucleotide probe complementary to the nucleic acid or a portion thereof labeled with an antigen; an antibody-peroxidase conjugate wherein the antibody is directed to the antigen; in admixture in an aqueous solution a hydroxyaryl cyclic diacylhydrazide compound of the formula:

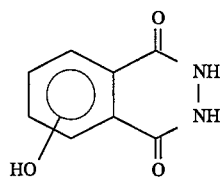

a phenolic enhancer compound in an amount which enhances light production from the diacylhydrazide in the presence of the peroxidase and decreases background chemiluminescence; a peroxide compound in an amount which reacts with the diacylhydrazide in the presence of the peroxidase; a chelating agent in an amount which prevents the peroxide compound from activating the diacylhydrazide prior to reaction with the peroxidase; and a water-soluble chemiluminescence-enhancing substance; and a surface, preferably a membrane, on which the hybridization is performed.

Finally, the present invention relates to a kit for detecting a protein comprising: an antibody-peroxidase conjugate wherein the antibody is directed to the protein or to a primary antibody directed to the protein; in admixture in an aqueous solution a hydroxyaryl cyclic diacylhydrazide compound of the formula:

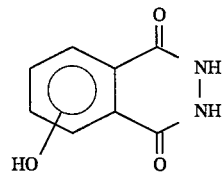

a phenolic enhancer compound in an amount which enhances light production from the diacylhydrazide in the presence of the peroxidase and decreases background chemiluminescence; a peroxide compound in an amount which reacts with the diacylhydrazide in the presence of the peroxidase; a chelating agent in an amount which prevents the peroxide compound from activating the diacylhydrazide prior to reaction with the peroxidase; a water-soluble chemiluminescence-enhancing substance; and a surface, preferably a membrane, on which the protein-antibody binding is performed.

The detection of chemiluminescence from the oxidation of a hydroxyaryl cyclic diacylhydrazide by hydrogen peroxide catalyzed by a peroxidase enzyme can be accomplished with good sensitivity. Enhancement of this reaction by incorporation of chemiluminescence-enhancing substances has permitted the measurement of chemiluminescence using still lower levels of the peroxidase enzyme. Coupling this enzyme to a biological molecule of interest then permits the detection of this biological molecule with great sensitivity.

A key consideration in developing ultrasensitive detection systems is to provide the largest signal possible through amplification while maintaining the lowest possible level of background signal in relation to the signal to be measured. For this purpose, additives have been discovered which suppress the generation of chemiluminescence from the reaction of hydrogen peroxide and hydroxyaryl cyclic diacylhydrazides in the absence of peroxidase enzymes.

The present invention involves a method of generating chemiluminescence from the oxidation of hydroxyaryl cyclic diacylhydrazides by the action of a peroxidase enzyme, a peroxide compound and enhancers. The invention also relates to the use of this method to detect the peroxidase enzyme with high sensitivity. Further, the invention relates to the use of the method to detect and quantitate various biological molecules which are bound to this enzyme by chemical bonds or through physical interactions. The intensity of the resulting chemiluminescence provides a direct measure of the quantity of labeled organic or biological molecule. For example, the method may be used to detect haptens, antigens and antibodies by the technique of immunoassay, proteins by Western blotting, DNA and RNA by Southern and Northern blotting, respectively. The method may also be used to detect DNA in DNA sequencing applications. The method may be used to detect hydrogen peroxide generated by enzymes such as glucose oxidase, glucose-6-phosphate dehydrogenase, galactose oxidase, galactose-6-phosphate dehydrogenase, and amino acid oxidase. The method may also therefore be used as a means to detect the enzymes mentioned above which generate hydrogen peroxide. Scheme 1

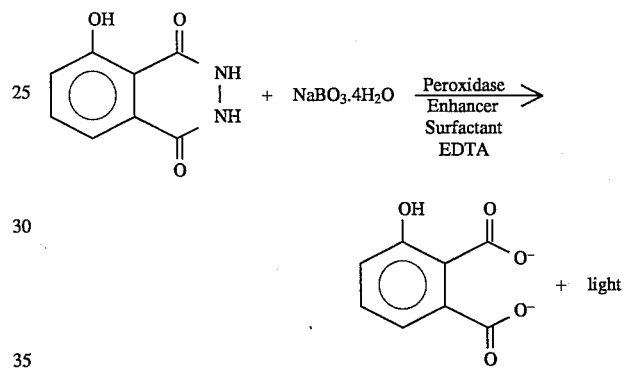

An important component of the invention is that a hydroxyaryl cyclic diacylhydrazide, a peroxide compound, a phenolic compound and a chelating agent such as EDTA may be combined in one solution and stored for later use without generating a large background chemiluminescent signal. This would not be expected in view of the fact that the combination of a hydroxyaryl cyclic diacylhydrazide and certain oxidants normally constitute a highly chemiluminescent reaction system.

An unexpected finding of the present invention is that incorporation of certain substituted phenol compounds in combination with surfactants into the reaction mixture decreases background chemiluminescence presence of added peroxidase. This is surprising in view of the fact that the substrate hydrazide is itself also a phenol. A second phenol would not a priori be expected to affect any enhancement. The combined suppressing of background chemiluminescence and enhancement of peroxidase-initiated chemiluminescence greatly extends the analytical range of use. Phenolic compounds found to enhance the amount of chemiluminescence produced in the reaction of hydroxyaryl cyclic diacylhydrazide with a peroxide compound and a peroxidase enzyme include, but are not limited to: p-phenylphenol, p-iodophenol, p-bromophenol, p-hydroxycinnamic acid, 6-bromo-2-naphthol, d-luciferin and 2-cyano-6-hydroxybenzothiazole. Selection of the best enhancer for a particular application will be based on performance, amount required, cost and availability.

The invention relates to a method for generating chemiluminescence by the action of a peroxidase enzyme or enzyme conjugate with a mixture containing a hydroxyaryl cyclic diacylhydrazide, a peroxide compound, an enhancer or catalyst and a suppressing agent in an aqueous buffer. The invention relates to a method for generating chemiluminescence by the action of a peroxidase enzyme or enzyme conjugate and a substrate for said peroxidase enzyme with a mixture containing a hydroxyaryl cyclic diacylhydrazide, a peroxide compound, a peroxidase enzyme, an enhancer or catalyst and a chelating agent in an aqueous buffer.

The invention also relates to the use of the method for the detection on solid supports or membranes such as nitrocellulose, nylon or polyvinylidene difluoride (PVDF) membranes, of proteins in Western blots, DNA in Southern blots and other DNA hybridization assays and RNA in Northern blots. For reasons which are not clear, the membrane significantly enhances the amount of light produced.

The present invention involves a solution in an aqueous buffer containing 1) a phenol enhancer, 2) a peroxide compound wherein the peroxide compound may be hydrogen peroxide, urea peroxide, or a perborate salt, 3) 5-hydroxy-2,3-dihydrophthalazine-1,4-dione, 4) a cation complexing agent wherein the agent may be selected from the group consisting of chelating agents such as ethylenediaminetetraacetic acid (EDTA), diethylenetriaminepentaacetic acid (DTPA), or ethylenebis(oxyethylenenitrilo)-tetraacetic acid (EGTA) and their salts, and 5) a surfactant chosen from either of two groups; the first group consisting of polymeric cationic surfactants selected from polymers bearing pendant phosphonium groups (such as described in U.S. Ser. No. 07/855,537, filed Mar. 20, 1992) or ammonium groups, the second group consisting of nonionic surfactants such as polyoxyethylenated alkylphenols, polyoxyethylenated alcohols, polyoxyethylenated ethers, polyoxyethylenated sorbitol esters and the like. It is anticipated that other hydroxyaryl cyclic diacylhydrazides may also be useful in practicing the present invention.

In a preferred method of practicing the present invention an aqueous buffer solution with a pH in the range of 8–10 containing 5-hydroxy-2,3-dihydrophthalazine-1,4-dione at a final concentration from about 0.01M to $1\times10^{-4}$M, a phenol compound such as p-iodophenol at a final concentration from about 0.01M to $1\times10^{-6}$M and a surfactant at a final concentration from about 1% to 0.01% (v/v) is mixed with a second solution in water or aqueous buffer containing a peroxide source such as hydrogen peroxide or, preferably, a perborate salt and a cation complexing agent such as EDTA at a final concentration from about $1\times10^{-3}$M to $1\times10^{-6}$M to form the detection reagent solution. This solution is contacted with the peroxidase enzyme which may either be in solution or adhered to a solid support. Optimum concentrations of reagents must be determined individually for each composition. The concentration of enhancer in particular should be optimized with care for each different enhancer used in order to produce the maximum enhancement of light emission. The choice of the polymeric surfactant is dictated by the application, especially by the membrane on which the chemiluminescent reaction is to be performed. A cationic surfactant and especially a phosphonium salt containing polymer is preferred when performing the reaction on nitrocellulose.

Significant advantages of hydroxyaryl cyclic diacylhydrazides and compositions of the present invention containing them is their stability toward thermal, hydrolytic and photochemical degradation and ease of purification. Aminoaryl cyclic diacylhydrazides such as luminol and compositions containing them are readily decomposed by room light leading to loss of sensitivity and poor reproducibility when used in chemiluminescence detection schemes (Y. Omote, H. Yamamoto, N. Sugiyama, Chem. Commun., 914 (1970)). Aminoaryl cyclic diacylhydrazides are difficult to prepare and maintain in a state of high purity and must either be protected from light or purified immediately before use (R. A. W. Stott, L. J. Kricka, in Bioluminescence and Chemiluminescence New Perspectives, J. Scholmerich et al, Eds., John Wiley & Sons, Chichester, England, 237–240 (1987)). Hydroxyaryl cyclic diacylhydrazides can be easily purified to a high degree by recrystallization and maintain their purity without special storage requirements. Aqueous solutions of 5-hydroxy-2,3-dihydrophthalazine-1,4-dione retain their activity after storage at ambient temperature and in room light for at least two months.

1. Chemiluminescent Detection of Proteins by Western Blot

Rabbit anti-goat IgG-peroxidase conjugate and rabbit anti-goat IgG-peroxidase were obtained from Cappel Products (Durham, N.C.). Human transferrin and fractionated goat anti-human transferrin serum were purchased from Sigma Chemical Co. (St. Louis, Mo.). The IgG sample was centrifuged at 10,000 g for two minutes and the supernatant was used in the immunological reaction. "IMMOBILON™-P" transfer membrane was obtained from Millipore Corp. (Bedford, Mass.). Kodak (Rochester, N.Y.) X-OMAT AR and OMC films were used in the assay procedure.

SDS-PAGE was performed utilizing the buffer system described by Laemmli (U. K. Laemmli, Nature (London), 227,680 (1970)). The stacking gel was 4.38% acrylamide:0.12% bisacrylamide. The separating gel was 6.81% acrylamide:0.19% bisacrylamide. Following electrophoresis the gel was equilibrated for 7–8 minutes with the transfer buffer which contained 20 mM Tris, 153 mM glycine and 20% (v/v) methanol. The gel, sandwiched between a sheet of transfer membrane and a sheet of chromatography paper 3MM (Whatman), was placed in the transfer unit (Bio-Rad Laboratories, Richmond, Calif.). The proteins in the gel were electroeluted for 50–60 minutes at 4° C. at a 100 V constant voltage. The membrane was then placed in 50 mM Tris-HCl buffered saline at pH 7.4 (TBS) at 4° C. overnight. After this period the membrane was washed with TBS for 15 minutes.

The membrane was treated with 0.05% Tween-20 in 50 mM Tris-HCl buffered saline at pH 7.4 (T-TBS) containing 1% non-fat powdered milk (NFM) for one hour at room temperature. This blocked membrane was incubated for 75 minutes at room temperature with primary antibody (1:500 dilution of goat anti-human transferrin IgG fraction) using T-TBS containing 1% NFM.

The membrane was then rinsed and washed three times for ten minutes each with T-TBS at room temperature. The washed membrane was incubated for one hour at room temperature with secondary antibody (1:25000 dilution of rabbit anti-goat IgG peroxidase conjugate) using T-TBS containing 1% NFM. The membrane was rinsed and washed four times for ten minutes each with T-TBS followed by a ten minute wash with TBS.

The washed membrane was soaked in a detection reagent solution containing a peroxide compound and 5-hydroxy-2,3-dihydrophthalazine-1,4-dione for ten minutes, drained, placed between sheets of transparency film. The X-ray film was exposed to the membrane for one to ten minutes and developed.

Composition of detection reagent solution:

| Solution A | |
|---|---|
| Tris buffer, pH 8.8 | 0.1 M |
| 5-hydroxy-2,3-dihydrophthala-zine-1,4-dione | $3.0 \times 10^{-3}$ M |
| p-iodophenol | $4.8 \times 10^{-3}$ M |
| Tween 20 | 1.0% (w/w) |
| Solution B | |
| Tris buffer, pH 8.8 | 0.1 M |
| $NaBO_3 \cdot 4H_2O$ | $6.5 \times 10^{-3}$ M |
| EDTA | $1 \times 10^{-4}$ M |

The reagent is prepared by mixing solutions A and B in a 1:1 ratio.

Figure 1B:
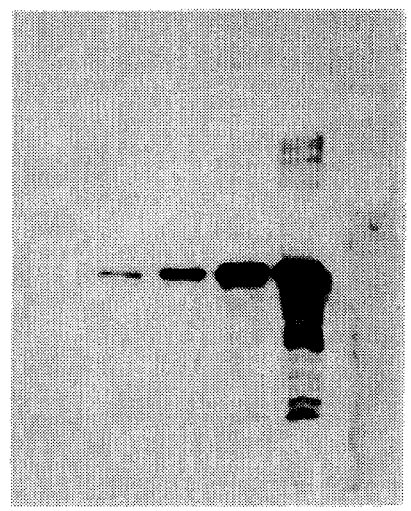

To determine the sensitivity of this detection system for Western blotting, a model system of transferrin was used to provide polypeptide bands in known quantities. The transferrin standards utilized were clearly visible down to 10 pg/slot without background after a one minute exposure to Kodak X-OMAT AR x-ray film (FIG. 1A) or after a ten minute exposure to OMC x-ray film (FIG. 1B). It was possible to make several exposures of the membrane during the first hour as the membrane continued to emit light.

Chemiluminescent detection of proteins on Western blots using the system of anti-goat IgG-peroxidase conjugate, peroxide and 5-hydroxy-2,3- dihydrophthalazine-1,4-dione is capable of detecting extremely small amounts of protein with very short exposure times. Under optimum conditions ten picograms of protein can be detected on x-ray film with an exposure time of one minute using X-OMAT AR or ten minutes using OMC.

2. Chemiluminescent Western Blot on Nitrocellulose Membrane

A Western blot analysis was performed according to the protocol described in Example 1 with the substitution of nitrocellulose membrane for PVDF and with a detection reagent solution prepared by mixing solutions A and B below in a 1:1 ratio. Bovine serum albumin was substituted for non-fat milk in the blocking solution.

| Solution A | |
|---|---|
| Tris buffer, pH 8.8 | 0.1 M |
| 5-hydroxy-2,3-dihydrophthalazine-1,4-dione | $3.0 \times 10^{-3}$ M |
| p-iodophenol | $4.8 \times 10^{-3}$ M |
| poly(vinylbenzyl)tributylphosphonium chloride-poly(vinylbenzyl)trioctylphosphonium-chloride copolymer | 0.05% (w/w) |
| (Tween 20) polyoxyethylene sorbitan monolaurate | 1.0% w/w |
| Solution B | |
| Tris buffer, pH 8.8 | 0.1 M |
| $NaBO_3 \cdot H_2O$ | $6.5 \times 10^{-3}$ M |
| EDTA | $1 \times 10^{-4}$ M |

3. Chemiluminescent Detection of DNA Dot Blots

"IMMOBILON™-P" (Millipore, Bedford, Mass.) was sequentially soaked in methanol for 40 seconds, in $H_2O$ for two minutes and in 6×SSC (20×SSC is 3M NaCl, 0.3M sodium citrate, pH 7.0) for five minutes. The membrane was placed on two thicknesses of 3 MM blotting paper (Whatman) containing 6× SSC. Biotinylated lambda DNA/Hind III fragments (Life Technologies, Inc., Bethesda, Md.) were diluted with 6×SSC containing 100 g/mL sheared herring sperm DNA (Boehringer-Mannheim, Indianapolis, Ind.) and 1.5 μL of each solution of DNA was dotted on the "IMMOBILON™-P" membrane or on nitrocellulose membrane (Schleicher & Schuell). Blots were air dried for 30 minutes and then baked for one hour at 80° C. Baked "IMMOBILON™-P" was sequentially soaked in methanol for ten seconds, in $H_2O$ for two minutes and in 50 mM Tris-HCl buffered saline at pH 7.4 (TBS) for ten minutes. Baked nitrocellulose membrane was sequentially soaked in $H_2O$ for two minutes and in TBS for five minutes.

The membranes were blocked with 0.05% Tween-20 in Tris-HCl buffered saline at pH 7.4 (T-TBS) containing 1% non-fat milk (NFM) for one hour at room temperature with gentle agitation and then raised twice with T-TBS. Blots were incubated with a 1:10,000 dilution of avidin-horseradish peroxidase (Cappel Research Products) in T-TBS for 15 minutes at room temperature with gentle agitation. The membrane was then rinsed four times for 15 minutes each with T-TBS followed by four rinses with $H_2O$. Excess solution was removed from the membrane, the membrane was transferred to a fresh container and then incubated with the reagent solution of Example 1 for five minutes. Excess detection reagent was drained off and the membrane was placed between transparency film (Arkwight, Inc.) followed by autoradiography using Kodak X-OMAT XAR 5 film.

Figure 3A:
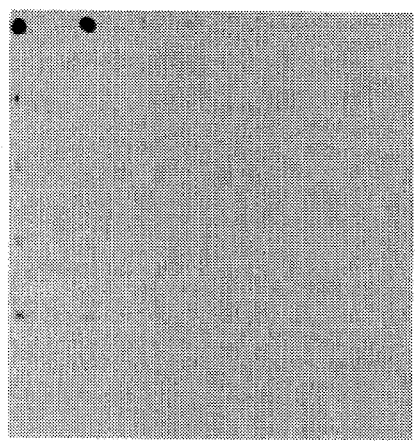
Figure 3B:
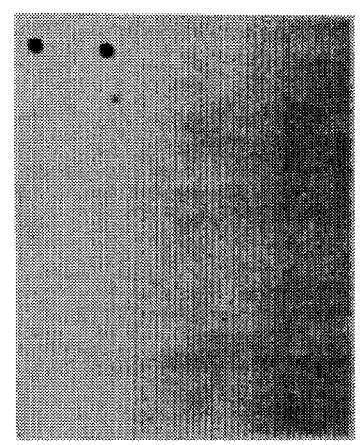

The DNA dot blots in FIG. 3 were performed with avidin-horseradish peroxidase and reagents of the present invention using (1) 15 ng, (2) 1.5 ng, (3) 150 pg, (4) 15 pg, (5) 1.5 pg and (6) 0 pg quantities of biotinylated lambda DNA/Hind III fragments each containing 150 ng herring sperm DNA. Spots of 15 ng biotinylated lambda DNA/Hind III fragments on nitrocellulose membrane produced stronger signals than the control spot containing 150 ng herring sperm DNA (FIG. 3A). The observed detection limit of at least 15 ng biotinylated lambda DNA dotted on nitrocellulose membrane was also obtained with dot blots on Immobilon™-P using this detection reagent (FIG. 3B). Longer x-ray film exposures were required when using Immobilon™-P with either detection reagent (data not shown) to achieve equivalent signal. These observations demonstrate that chemiluminescent detection of DNA dot blots utilizing reagents of the present invention yield excellent sensitivity with short exposure times.

4. Chemiluminescent Detection of Southern Blots

Mouse genomic DNA (Clontech Laboratories, Inc., Palo Alto, Calif.) was cleaved to completion with restriction endonuclease EcoR1 (Boehringer-Mannheim, Indianapolis, Ind.) at a concentration of 50 μg/mL. The restricted DNA was purified by extraction once with phenol/chloroform, once with chloroform and was precipitated with ethanol. The purified DNA was separated by 0.8% agarose gel electrophoresis. The electrophoresis buffer was 40 mM Tris-acetate and 2 mM EDTA (pH 8.0). After electrophoresis the gel was rinsed with $H_2O$ and then soaked in 0.25 N HCl for 12 minutes with gentle agitation. The gel was once again rinsed with $H_2O$ and incubated twice in 0.4M NaOH/0.6M NaCl for 15 and 20 minutes, respectively.

"IMMOBILON™-P" was soaked sequentially in methanol, $H_2O$ and 0.4 M NaOH/0.6M NaCl for 40 seconds, 2 and 10 minutes, respectively. The DNA in the alkaline treated agarose gel was transferred onto alkaline treated "IMMOBILON™-P" by capillary blotting overnight using 0.4M NaOH/0.6M NaCl. The membrane was neutralized by agitation in 0.75M NaCl/0.5M Tris-HCl (pH 7.5) for 10 minutes at room temperature followed by agitation in 6×SSC (20×SSC is 3M NaCl, 0.3M sodium citrate, pH 7.0) three times for five minutes each at room temperature. The blots were air-dried on 3 MM blotting paper for two hours. The membrane was UV-irradiated for two minutes with a Fotodyne Model 3–3000 illuminator at a distance of 20 cm.

The membrane was soaked in methanol for five seconds and then in H$_2$O for two minutes to remove air in the membrane, followed by prehybridization using hybridization buffer ("AMERSHAM #RPN.3000", Amersham International, PLC, Amersham, England) containing 0.5 M NaCl and blocking agents (Amersham #RPN.3000) for 60 minutes at 42° C. The hybridization probe, v-mos DNA (Clontech Lab. Inc., Palo Alto, Calif.) was labeled with horseradish peroxidase (Cappel, Durham, N.C.) according to the manufacturer's instructions and the hybridization proceeded overnight at 42° C. using a hybridization buffer containing 0.5M NaCl, blocking agents and 300 ng/mL horseradish peroxidase labeled v-mos DNA. The membrane was washed sequentially with 0.5×SSC/0.4% SDS twice for five minutes each at room temperature, with 0.5×SSC/0.4% SDS three times for ten minutes each at 55° C., with 2×SSC twice for five minutes each at room temperature and then with H$_2$O another four times. The membrane was placed on 3 MM blotting paper for one minute to remove excess solution, then transferred to a clean container followed by the addition of the detection reagent of Example 1. After a one minute incubation, excess solution was drained off and the blots were placed between sheets of transparency film followed by exposure to Kodak X-OMAT XAR 5 film for 2 minutes.

Figure 4:

The reagent of the present invention can be used to detect a single copy gene in mouse genomic DNA as shown in FIG. 4. The v-mos probe, which is complementary to the proto-oncogene mos, was hybridized to Southern blotted mouse genomic DNA. The target restriction fragment is 1.4 kd providing 8.4 pg ($1.1 \times 10^{-17}$ moles) of target DNA in the 20 μg leading tracks. Close examination of the x-ray film indicates that two additional bands can be found in lanes 1 and 2. The artifactual bands could possibly be associated with alkaline transfer. Lambda DNA/Hind III fragments were visible using the reagent of the present invention. The amount of each Hind III fragment is at least 470 times higher than that of the single copy gene. High levels of DNA fragments should yield non-specific signals in Southern blots using this detection reagent. This conclusion is supported by the results from the DNA dot blots described above. It is apparent that a single copy gene can be clearly detected using this detection reagent after a short exposure to x-ray film.

It will be appreciated that the foregoing examples are illustrative only and are not taken to be limiting unless so stated. Those skilled in the art will recognize that modifications and variations of the examples described above can be made without departing from the spirit of the invention. The present invention is limited only by the claims appended below.

The term surfactant indicates a water-soluble surface active agent selected from cationic, non-ionic, zwitterionic, and anionic compounds. Included are poloxyethylene glycol ethers, ammonium and phosphonium salts and the like.

We claim:

1. In a method for detecting a member of a specific binding pair labeled with a peroxidase enzyme in an assay procedure by a chemiluminescent reaction, the improvement which comprises the chemiluminescent reaction caused by:

(a) reacting with the binding pair on a surface a hydroxyaryl cyclic diacylhydrazide of the formula:

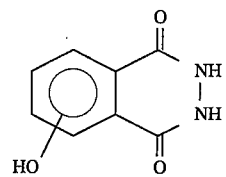

a phenolic enhancer compound in an amount which enhances light production from the diacylhydrazide in the presence of the peroxidase and decreases background chemiluminescence and a peroxide so that light is produced for detecting the member of the specific binding pair.

2. The method of claim 1 wherein the specific binding pair consists of a nucleic acid and an oligonucleotide probe which is complementary to and binds to the target nucleic acid or some portion thereof, wherein the probe is associated with the peroxidase enzyme either through a covalent bond, physical attractions, or by linkage through an enzyme-labeled specific binding pair.

3. The method of claim 2 wherein the nucleic acid is DNA.

4. The method of claim 2 wherein the nucleic acid is RNA.

5. The method of claim 2 wherein the peroxidase enzyme is horseradish peroxidase.

6. The method of claim 5 additionally consisting of the step of (a) hybridizing the nucleic acid and labeled oligonucleotide probe directly labeled with the horseradish peroxidase to form the binding pair, and (b) reacting the binding pair with the hydroxyaryl cyclic diacylhydrazide and a peroxide so that light is produced.

7. The method of claim 2 additionally consisting of (a) hybridizing the nucleic acid and labeled oligonucleotide probe to form the binding pair, (b) reacting the binding pair with a substance which strongly binds to the pair and which is bound to the peroxidase enzyme to form a bound enzyme conjugate, and (c) reacting the bound enzyme conjugate with a hydroxyaryl cyclic diacylhydrazide and a peroxide so that light is produced.

8. The method of claim 7 wherein the binding pair contains biotin and the substance is selected from the group consisting of an avidin-horseradish peroxidase conjugate and a streptavidin-peroxidase conjugate.

9. The method of claim 7 wherein the pair contains an antigenic site and the substance is an antibody-peroxidase conjugate which binds to the site.

10. The method of claim 1 wherein the specific binding pair consists of an antigen and an antibody which binds to the antigen.

11. The method of claim 10 wherein the antigen or antibody is associated with a peroxidase enzyme either through a covalent bond, physical attractions, or by linkage through an enzyme-labeled specific binding pair.

12. The method of claim 11 wherein the enzyme is horseradish peroxidase.

13. The method of claim 12 additionally consisting of (a) forming an antigen-antibody complex and (b) reacting the antigen-antibody complex which is labeled with a peroxidase enzyme with the hydroxyaryl cyclic diacylhydrazide and a peroxide so that light is produced.

14. The method of claim 11 additionally consisting of (a) forming an antigen-antibody complex; and (b) reacting the labeled antigen-antibody complex with a substance which strongly binds to the pair and is bound to a peroxidase enzyme, and (c) reacting the bound enzyme conjugate with the hydroxyaryl cyclic diacylhydrazide and a peroxide so that light is produced.

15. The method of claim 14 wherein the pair is labeled with biotin and the substance is selected from the group consisting of an avidin-peroxidase conjugate and streptavidin-peroxidase conjugate.

16. The method of claim 14 wherein the pair is labeled with a second antigen which reacts with the antibody and the label-binding substance is a conjugate between a peroxidase enzyme and an antibody to the second antigen.

17. The method of any one of claims 1, 6, 7, 13 or 14 wherein the light is produced in a reaction using the peroxidase enzyme and the hydroxyaryl cyclic diacylhydrazide in a composition which comprises:

the hydroxyaryl cyclic diacylhydrazide; a phenolic compound which enhances light production from the diacylhydrazide and decreases light production from the diacylhydrazide in the absence of the peroxidase; a peroxide compound which reacts with the diacylhydrazide in the presence of the peroxidase; a chelating agent which prevents the peroxide compound from activating the diacylhydrazide prior to the addition of the peroxidase to the composition; and a water-soluble surfactant compound which acts to enhance the light production.

18. The method of claim 17 wherein the water-soluble surfactant compound is a non-ionic surfactant.

19. The method of claim 17 wherein the water-soluble surfactant is a cationic polymer.

20. The method of claim 19 wherein the cationic polymer is a polymeric phosphonium salt selected from poly(vinylbenzyl)trialkylphosphonium salts.

21. The method of claim 19 wherein the cationic polymer is a polymeric ammonium salt selected from poly(vinylbenzyl)trialkylammonium salts.

22. The method of any one of claims 1, 6, 7, 13 or 14 wherein the hydroxyaryl cyclic diacylhydrazide is 5-hydroxyphthalazine-1,4-dione.

23. The method of claim 1 wherein the surface is selected from the group consisting of nylon, nitrocellulose and polyvinylidene difluoride membranes.

24. The method of any one of claims 1, 6, 7, 13 or 14 wherein the light produced is detected on a photographic film.

25. A kit for detecting a nucleic acid or a fragment of a nucleic acid comprising:
    (a) an oligonucleotide probe complementary to the nucleic acid or a portion thereof labeled with a peroxidase enzyme;
    (b) a hydroxyaryl cyclic diacylhydrazide of the formula:

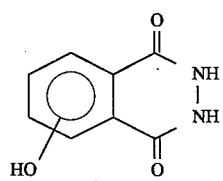

a phenolic enhancer compound in an amount which enhances light production from the diacylhydrazide in the presence of the peroxidase enzyme and decreases background chemiluminescence;
    (c) a peroxide compound in an amount which reacts with the diacylhydrazide in the presence of the peroxidase;
    (d) a chelating agent in an amount which prevents the peroxide compound from activating the diacylhydrazide prior to reaction with the peroxidase; and a water-soluble chemiluminescence-enhancing surfactant; and
    (e) a membrane on which the hybridization is performed.

26. A kit for detecting a nucleic acid or a fragment of a nucleic acid comprising:
    (a) an oligonucleotide probe complementary to the nucleic acid or a portion thereof labeled with biotin;
    (b) a streptavidin-peroxidase or avidin-peroxidase conjugate;
    (c) in admixture in an aqueous solution a hydroxyaryl cyclic diacylhydrazide compound of the formula:

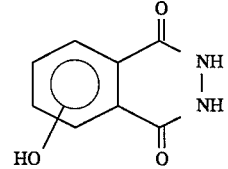

a phenolic enhancer compound in an amount which enhances light production from the diacylhydrazide in the presence of the peroxidase and decreases background chemiluminescence; a peroxide compound in an amount which reacts with the diacylhydrazide in the presence of the peroxidase; a chelating agent in an amount which prevents the peroxide compound from activating the diacylhydrazide prior to reaction with the peroxidase; and a water-soluble chemiluminescence-enhancing surfactant; and
    (d) a membrane on which the hybridization is performed.

27. A kit for detecting a nucleic acid or a fragment of a nucleic acid comprising:
    (a) an oligonucleotide probe complementary to the nucleic acid or a portion thereof labeled with an antigen; an antibody-peroxidase conjugate wherein the antibody is directed to the antigen;
    (b) in admixture in an aqueous solution a hydroxyaryl cyclic diacylhydrazide compound of the formula:

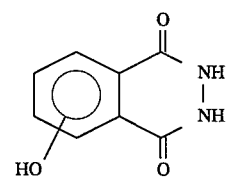

a phenolic enhancer compound in an amount which enhances light production from the diacylhydrazide in the presence of the peroxidase and decreases background chemiluminescence; a peroxide compound in an amount which reacts with the diacylhydrazide in the presence of the peroxidase; a chelating agent in an amount which prevents the peroxide compound from activating the diacylhydrazide prior to reaction with the peroxidase; and a water-soluble chemiluminescence-enhancing surfactant; and
    (b) a membrane on which the hybridization is performed.

28. A kit for detecting a protein comprising:
    (a) an antibody-peroxidase conjugate wherein the antibody is directed to the protein or to a primary antibody directed to the protein;
    (b) in admixture in an aqueous solution a hydroxyaryl cyclic diacylhydrazide compound of the formula:

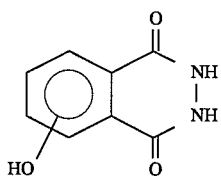

a phenolic enhancer compound in an amount which enhances light production from the diacylhydrazide in the presence of the peroxidase and decreases background chemiluminescence; a peroxide compound in an amount which reacts with the diacylhydrazide in the presence of the peroxidase; a chelating agent in an amount which prevents the peroxide compound from activating the diacylhydrazide prior to reaction with the peroxidase; a water-soluble chemiluminescence-enhancing surfactant; and (c) a membrane on which the protein-antibody binding is performed.

29. A kit for detecting a protein comprising:

(a) a primary antibody directed to the protein; a peroxidase-secondary antibody conjugate directed to the primary antibody;

(b) in admixture in an aqueous solution a hydroxyaryl cyclic diacylhydrazide compound of the formula:

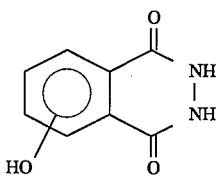

a phenolic enhancer compound in an amount which enhances light production from the diacylhydrazide in the presence of the peroxidase and decreases background chemiluminescence; a peroxide compound in an amount which reacts with the diacylhydrazide in the presence of the peroxidase; a chelating agent in an amount which prevents the peroxide compound from activating the diacylhydrazide prior to reaction with the peroxidase; a water-soluble chemiluminescence-enhancing surfactant and a membrane on which the protein-antibody binding is performed.

30. The kit of any of claims 25 to 29 wherein the hydroxyaryl cyclic diacylhydrazide compound is 5-hydroxy-2,3-dihydrophthalazine-1,4-dione.

31. The kit of any of claims 25 to 29 wherein the water-soluble chemiluminescence-enhancing surfactant is a non-ionic surfactant.

32. The kit of any of claims 25 to 29 wherein the water-soluble chemiluminescence-enhancing surfactant is a cationic polymer.

33. The kit of claim 32 wherein the cationic polymer is a polymeric phosphonium salt.

34. The kit of claim 32 wherein the cationic polymer is a polyvinylbenzyl trialkylphosphonium salt.

35. The kit of claim 32 wherein the cationic polymer is a polymeric ammonium salt.

36. The kit of claim 32 wherein the cationic polymer is a polyvinylbenzyl trialkylammonium salt.

37. The method of claim 1 wherein the phenolic enhancer compound is selected from the group consisting of p-phenylphenol, p-iodophenol, p-bromophenol, p-hydroxycinnamic acid, 6-bromo-2-naphthol, d-luciferin and 2-cyano-6-hydroxybenzothiazole.

38. The method of claim 17 wherein the phenolic enhancer compound is selected from the group consisting of p-phenylphenol, p-iodophenol, p-bromophenol, p-hydroxycinnamic acid, 6-bromo-2-naphthol, d-luciferin and 2-cyano-6-hydroxybenzothiazole.

39. The method of any of claims 25 to 29 wherein the phenolic enhancer compound is selected from the group consisting of p-phenylphenol, p-iodophenol, p-bromophenol, p-hydroxy-cinnamic acid, 6-bromo-2-naphthol, d-luciferin and 2-cyano-6-hydroxybenzothiazole.

* * * * *

UNITED STATES PATENT AND TRADEMARK OFFICE
CERTIFICATE OF CORRECTION

PATENT NO. : 5,601,977
DATED : February 11, 1997
INVENTOR(S) : Hashem Akhavan-Tafti and Richard S. Handley It is certified that error appears in the above-indentified patent and that said Letters Patent is hereby corrected as shown below:

Column 9, line 66, "g/mL" should be --µg/mL--.

Column 16, line 34 (Claim 39), "method" should be --kit--.

Signed and Sealed this

Twenty-seventh Day of May, 1997

Attest:

BRUCE LEHMAN

Attesting Officer    Commissioner of Patents and Trademarks